US010899019B2

(12) United States Patent
Regnier et al.

(10) Patent No.: US 10,899,019 B2
(45) Date of Patent: Jan. 26, 2021

(54) MECHATRONIC FORCEPS

(71) Applicants: PERCIPIO ROBOTICS, Besancon (FR); SORBONNE UNIVERSITE, Paris (FR); CENTRE NATIONAL DE LA RECHERCHE SCIENTIFIQUE (C.N.R.S), Paris (FR)

(72) Inventors: Stephane Regnier, Bois Colombes (FR); Thomas Daunizeau, Paris (FR); Dogan Sinan Haliyo, Paris (FR); Tianming Lu, Ivy sur Seine (FR); Marie Lutringer, Geneuille (FR); David Heriban, Ecole Valentin (FR)

(73) Assignees: PERCIPIO ROBOTICS, Besancon (FR); SORBONNE UNIVERSITE, Paris (FR); CENTRE NATIONAL DE LA RECHERCHE SCIENTIFIQUE (C.N.R.S.), Paris (FR)

( * ) Notice: Subject to any disclaimer, the term of this patent is extended or adjusted under 35 U.S.C. 154(b) by 94 days.

(21) Appl. No.: 16/314,959

(22) PCT Filed: Jul. 3, 2017

(86) PCT No.: PCT/FR2017/051790
§ 371 (c)(1),
(2) Date: Jan. 3, 2019

(87) PCT Pub. No.: WO2018/007733
PCT Pub. Date: Jan. 11, 2018

(65) Prior Publication Data
US 2019/0308330 A1    Oct. 10, 2019

(30) Foreign Application Priority Data

Jul. 4, 2016 (FR) .................................. 16 56359

(51) Int. Cl.
B25J 15/02 (2006.01)
B25J 7/00 (2006.01)
(Continued)

(52) U.S. Cl.
CPC ............... *B25J 15/02* (2013.01); *A61B 17/30* (2013.01); *B25B 9/02* (2013.01); *B25J 7/00* (2013.01);
(Continued)

(58) Field of Classification Search
CPC ......... A61B 34/70; A61B 34/72; A61B 17/29; A61B 2017/00398; A61B 2017/2944;
(Continued)

(56) References Cited

U.S. PATENT DOCUMENTS 5,332,275 A * 7/1994 Conway ..................... B25J 7/00
294/100
6,691,586 B2 * 2/2004 Muramatsu ............ A61B 17/30
294/100
(Continued)

FOREIGN PATENT DOCUMENTS

CH      685749 A5    9/1995
DE   19782304 B4   10/2007
(Continued)

*Primary Examiner* — Stephen A Vu
(74) *Attorney, Agent, or Firm* — Volpe Koenig (57) ABSTRACT

A mechatronic device includes two arms extending from a base in a first direction and shaped to be handheld by an operator, the two arms having free ends forming a gripper and arranged to move closer together by rotation from a rest position to an active position, a motor housed in the base, an actuator mounted between the arms, and a means for controlling said actuator, the actuator connected to the motor so as to be driven in movement in translation in the first direction. The actuator also has a first contact surface that forms a cam with a respective second contact surface on
(Continued)

each arm, the first contact surface remaining engaged with the second contact surface. The control means controls the movement in translation of the actuator to produce a movement in rotation of the arms that applies a chosen force of the gripper in its active position.

11 Claims, 3 Drawing Sheets (51) Int. Cl.
*B25B 9/02* (2006.01)
*A61B 17/30* (2006.01)
*A61B 17/00* (2006.01)
*A61B 34/00* (2016.01)
*A61B 90/00* (2016.01)

(52) U.S. Cl.
CPC ..... *A61B 34/72* (2016.02); *A61B 2017/00398* (2013.01); *A61B 2017/305* (2013.01); *A61B 2090/064* (2016.02)

(58) Field of Classification Search
CPC .............. A61B 17/30; A61B 2017/305; A61B 2090/064; B25J 15/02; B25J 7/00; B25B 9/02

See application file for complete search history.

(56) References Cited

U.S. PATENT DOCUMENTS

| 7,269,892 | B2 * | 9/2007 | Miyazaki | B23K 3/0369 |
| | | | | 29/739 |
| 7,456,642 | B2 * | 11/2008 | Saulnier | G01R 1/06788 |
| | | | | 324/755.05 |
| 7,631,913 | B2 * | 12/2009 | Mochizuki | G02B 21/32 |
| | | | | 294/103.1 |
| 2003/0110874 | A1 | 6/2003 | Muramatsu | |
| 2017/0027598 | A1 | 2/2017 | Hernandez Juanpera | |

FOREIGN PATENT DOCUMENTS

| EP | 1334700 A1 | 8/2003 |
| EP | 1584414 A1 | 10/2005 |
| EP | 1627707 A1 | 2/2006 |
| WO | 2015/158945 A1 | 10/2015 |

* cited by examiner

MECHATRONIC FORCEPS

FIELD OF THE INVENTION

The present invention relates to a mechatronic gripper.

BACKGROUND

Nowadays the manipulation of macroscopic and microscopic objects finds its application in numerous technological fields, notably including electronics, medicine and the clockmaking industry.

The miniaturization of objects requires evolution of manipulation devices such as micromanipulation grippers and robotic grippers. In fact, there is a need for grippers to be able to carry out more and more precise manipulations.

There exist grippers comprising mechanisms to assist manipulation by the operators. These conventionally employ motorized systems to open and close the arms of a gripper. The grippers generally include a control element of the joystick type.

The document WO 2015/158945 discloses a gripper comprising arms driven by a motor. The arms are arranged parallel to one another. This arrangement is preserved on opening and closing the arms.

When manipulation concerns objects on a micrometric scale, manual operation by operators is impossible. A robotic system is employed to control this type of manipulation. However, the intervention of robotic systems requires human-machine interfaces. Those interfaces are rarely intuitive and make control of the gripper difficult. Moreover, physical phenomena encountered at the micrometric scale (surface adhesion effects, etc.) are nothing but difficult or even possible to control.

Moreover, with the prior art solutions, manipulation of objects on the submillimeter scale by an operator is difficult, or even impossible. Prior art devices are generally bulky. Size constraints are not complied with and do not meet the requirements of operators. Moreover, prior art devices are not satisfactory in energy terms.

The present invention aims to improve on this situation.

SUMMARY

To this end, the invention proposes a mechatronic device comprising two arms extending generally from a base in a first direction and shaped so as to be handheld by an operator, the two arms comprising free ends forming a gripper and arranged to move closer together, by rotation, from a rest position to an active position, a motor housed in the base, an actuator mounted between the arms, and a means for controlling said actuator, the actuator being connected to the motor in a such a way as to be moved in translation in the first direction, the actuator having at least one first contact surface arranged to form a cam with at least one second respective contact surface situated on each arm, the first contact surface or surfaces remaining engaged with the respective second contact surface or surfaces, the means for controlling the actuator being arranged to control said translation movement of the actuator in order to produce a rotational movement of said arms, that applies a chosen force of the gripper in its active position.

This is a portable and active mechatronic gripper. The mechatronic gripper is such that the holding force perceived by the operator can be decoupled from the force resulting from grasping an object.

In accordance with one embodiment, the chosen force may be selected from a force opposing rotation toward one another of said free ends. This is notably a question of a resistance perceived by the operator when grasping an object. In accordance with another embodiment, the chosen force may be a force assisting rotation toward one another of said free ends. This is notably a question of assistance perceived by the operator when grasping an object.

The mechatronic gripper according to the invention therefore offers a plurality of operating modes and advantages when used by an operator. Very particularly, the mechatronic gripper enables perception of a force opposing the closing of the gripper without any physical object being manipulated. The mechatronic gripper also enables to grasp an object without having to exert a closing force with the fingers. To these extreme examples of operation are added all intermediate operations in which the grasping and holding forces are non-zero forces (but nevertheless always decorrelated). Moreover, the mechatronic gripper enables simulation of grasping an object without a physical object actually being grasped (virtual object grasping). The mechatronic gripper can also be used in an automatic and/or robotic manner. Incidentally, the mechatronic gripper can also be employed as a conventional gripper if the active system according to the invention is deactivated (i.e. when the chosen force is zero).

In practice, the force perceived by the operator, namely the force that results from picking up and holding the gripper, is rendered independent of the force resulting from grasping an object using the active mechanism of the mechatronic gripper.

The actuator according to the invention is advantageously disposed on a longitudinal axis of the mechatronic gripper. This is advantageously the central longitudinal axis of the mechatronic gripper. This makes it possible to minimize the forces necessary to act on the rotation of the arms.

The movement of the actuator in translation in the first direction can be chosen from a movement of the actuator on the longitudinal axis in the first direction of that axis and a movement of the actuator on the longitudinal axis in the second direction of that axis. In practice, this is a question of pushing or pulling the actuator, enabling the gripper to be respectively opened and closed by rotation of the arms. An advantage of movements substantially along the longitudinal axis is notably the symmetry of movement in rotation of the arms, as well as minimizing the forces necessary to act on the rotation.

The actuator may comprise a ball-screw. An advantage of using a ball-screw is notably its bidirectionality. Moreover, the ball-screw used by the invention has the advantage of very low friction. To this is added the fact that the helix angle is large, which offers high efficiency and consequently good reversibility. Finally, the ball-screw has a high diameter to length ratio, which ensures good stiffness. This is favorable with regard to the bandwidth, i.e. with regard to the maximum frequency of the chosen force. The bandwidth substantially depends on the nature of the actuator as well as the stiffness and the mass of the components of the kinematic chain. The stiffer and lighter those elements, the greater the bandwidth. This is notably of benefit for an application with a view to creating tactile signals. Human fingers are high-performance sensors capable of sensing/measuring frequencies up to 500 Hz. In order to cover the entirety of the haptic spectrum, the mechatronic gripper has provision for exciting the fingers of the operator up to that frequency.

The actuator may be connected to the motor by means of a flexible coupling member. An advantage of this embodiment is notably the flexibility of construction. In fact, the flexible coupling member makes it possible to alleviate potential deviations relative to the longitudinal axis during assembly of the mechatronic gripper.

In one embodiment, the actuator comprises one or more rotatably mounted rollers, each roller forming said first contact surface. In this embodiment each arm comprises one or more shoulders projecting toward the opposite arm, each shoulder forming the respective second contact surface.

In another embodiment, the actuator comprises one or more inclined planes, each inclined plane forming said first contact surface. In this embodiment each arm comprises one or more rotatably mounted rollers, each roller forming the respective second contact surface.

In any of the aforementioned embodiments, respectively comprising a set of roller(s)/shoulder(s) and a set of inclined plane(s)/roller(s), a cam is formed in order to transform the movement in translation of the actuator into a movement in rotation of the arms of the mechatronic gripper. An advantage of this arrangement is that the cam in accordance with the invention has very low friction stresses.

The synergy that exists between a plurality of components of the mechatronic gripper in terms of minimizing friction should be noted. This has a number of advantages and notably in terms of manipulation, ergonomics, as well as in terms of saving energy.

The mechatronic gripper of the invention is such that the first contact surface or surfaces and the respective second contact surface or surfaces remain engaged. To this end, the mechatronic gripper of the invention may comprise a first magnetic component in the vicinity of the first contact surface or surfaces and a second magnetic component in the vicinity of the second contact surface or surfaces. The first and second magnetic components attract each other so as to bring about at least partially the situation of engagement between the first contact surface or surfaces and the respective second contact surface or surfaces.

In this embodiment, each assembly forming a cam therefore uses a magnetic field the force of which presses the roller(s) onto the shoulder(s) or inclined plane(s). This notably has the advantage of guaranteeing the transmission of movement of the actuator to the arms, and vice versa where necessary. The push and pull forces on the actuator are transmitted on the arms to engage rotation thereof.

The first and second magnetic components may comprise independently of each other a permanent magnet, a ferromagnetic body and/or an electromagnet. A magnetic circuit may advantageously be constructed around the cams by means of one or more permanent magnets and/or ferromagnetic cores/receivers. This arrangement notably results in a transmission mechanism generally making it possible to prevent any separation or offset between the first contact surface(s) and the respective second contact surface(s).

In one embodiment, the chosen force of the mechatronic gripper according to the invention may have a value between −50 N and 50 N, preferably between −30 N and 30 N. The force measurement is deduced from a measurement of the current in the winding of the motor. In any event, in active use the chosen force is always non-zero ($\neq 0$ N).

In one embodiment, the control means of the mechatronic device according to the invention comprise a predefined force database stored in a memory. In this embodiment the chosen force may be selected from those predefined forces. The database may be able to evolve and comprise data measured and collected during use of the gripper. A notable advantage is the simulation of forces engaged when manipulating virtual objects with the mechatronic gripper.

In one embodiment the ends of the arms may comprise interchangeable tips. This offers numerous advantages, such as using tips specifically adapted for given objects or replacing the tips if they break.

In one embodiment, the mechatronic device of the invention may comprise one or more sensors. The sensor(s) may be force sensors for measuring the forces applied when using the gripper or speed sensors, position sensors, temperature sensors, acceleration sensors or magnetic sensors. The advantage is notably the measurement of data in real time when using the device according to the invention. This notably makes it possible to control and to act in real time on the chosen force with the control means. Moreover, the sensors enable construction of the database relating to the use of the gripper according to the invention.

BRIEF DESCRIPTION OF THE DRAWINGS

Other advantages and features of the invention will become apparent on reading the following detailed description and from the appended drawings, in which.

DETAILED DESCRIPTION OF THE PREFERRED EMBODIMENTS

The drawings and the following description essentially contain elements of a certain character. They form an integral part of the description, and could therefore serve not only to provide a better understanding of the present invention but also to contribute to its definition, if necessary.

To develop a gripper capable of overcoming the problems of the prior art, the Applicant has turned to mechatronics. Mechatronics is a multidisciplinary field that combines techniques of mechanical engineering, electronics, automatic control and computer science.

The French standard NF E 01-010 gives the following definition of mechatronics: approach aiming at the synergistic integration of mechanical engineering, electronics, automatic control and computer science in the design and manufacture of the product with a view to increasing and/or optimizing its functionality.

The Applicant has developed a gripper capable of transmitting to an operator a holding force decorrelated from the reaction force of the manipulated object. Reciprocally, the gripper is able to grasp an object with a force independent of that exerted by the fingers of the operator. The gripper of the invention moreover guarantees natural use. The constraints on the mechanical design have been overcome. The gripper of the invention offers excellent reversibility, great compactness, low mass and low electrical energy consumption compared to prior art solutions.

Figure 1:
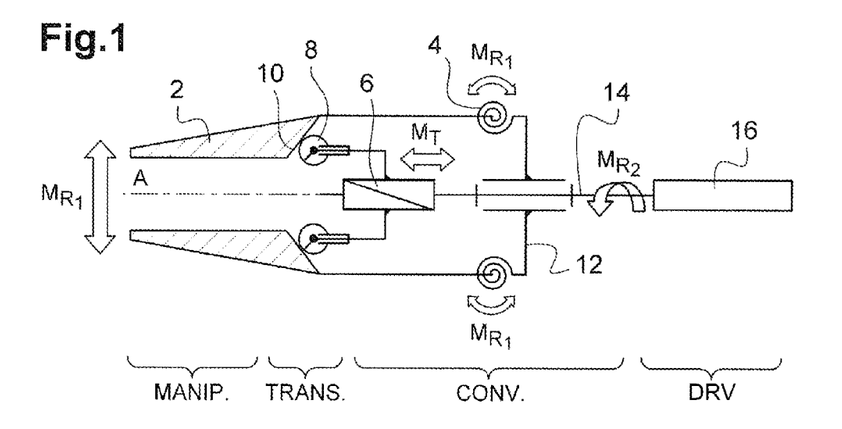
FIG. 1 is a functional schematic of a mechatronic device according to the invention.

FIG. 1 shows a functional schematic of a mechatronic device according to the invention. The general appearance of the device is that of straight tweezers. The device therefore has general symmetry with respect to a central longitudinal axis A. The mechanical architecture is symmetrical.

Two arms 2 are arranged on respective opposite sides of the axis A. The arms 2 are mounted so as to be able to be moved toward each other by a rotation movement MR1. To this end, each arm is fixed to a frame 12 by a rotation point (or pivot point) 4. The free ends of the arms can therefore be moved toward each other to form a gripper.

The rotation MR1 of the arms 2 is reversible. The movement of the arms 2 is from a rest position to an active position. The rest position corresponds to a situation in which no stress is applied to the arms 2. Any deviation from the rest position is an active position. For example, any situation with the arms 2 close together is an active position. In the rest position, no active stress is exerted at the rotation point 4. In the active position, a variable force stress is exerted at the rotation point 4. The arrangement of the mechatronic device enables it to be handheld in a similar way to holding in the hand standard tweezers.

The mechatronic device comprises a motor 16. The motor 16 is adapted to drive an actuator 6. The coupling member 14 is optionally disposed between the motor 16 and the actuator 6. The coupling member 14 is preferably flexible (also referred to as a flexible coupling) so as to be able to compensate any deviations from the axis A between the motor 16 and the actuator 6.

The motor 16 is adapted to engage a movement in rotation MR2 generating a movement in translation MT at the level of the actuator. To this end, the actuator 6 is adapted to transform the movement in rotation MR2 engaged by the motor 16 into movement in translation MT. Actuators comprising screw and nut type systems notably enable transformation of a movement in rotation (screw) into a movement in translation (nut).

In another mode of operation, the motor 16 can directly engage a movement in translation at the level of the actuator, without necessitating any movement transformation.

The actuator 6 comprises at least one first contact surface 8. Each arm 2 comprises at least one second contact surface 10. Each first contact surface 8 is in contact with a respective second contact surface 10. The assembly of the first contact surface(s) 8 and the second contact surface(s) 10 forms a cam. The cam enables transformation of movement in translation MT of the actuator 6 into movement in rotation MR1 of the arms.

Each first contact surface 8 and each respective second contact surface 10 remain engaged at all times. Thus, pulling by the actuator 6 (along the axis A in a direction toward the frame 12 in FIG. 1) has the consequence of movement of the two arms toward each other. Conversely, pushing by the actuator 6 (along the axis A in a direction toward the ends of the arms 2 in FIG. 1) has the consequence of moving the two arms away from each other.

The mechatronic device generally has four functional parts:
- a driving part DRV. notably comprising the element or elements able to engage a driving force, such as a motor 16 and the associated elements such as a driveshaft and a power supply (a battery, for example);
- a conversion part CONV. notably comprising the element or elements enabling transformation of the driving movement of the motor into movement in translation of the actuator 6, such as a part of the screw/nut type actuator 6;
- a transmission part TRANS. notably comprising the part or parts enabling engagement of movement of the arms based on movement in translation of the actuator 6, such as the first contact surface 8 and the second contact surface 10; and
- a manipulation part MANIP. notably comprising the part or parts capable of holding an object, such as the ends of the arms 2 forming a gripper.

Figure 2:
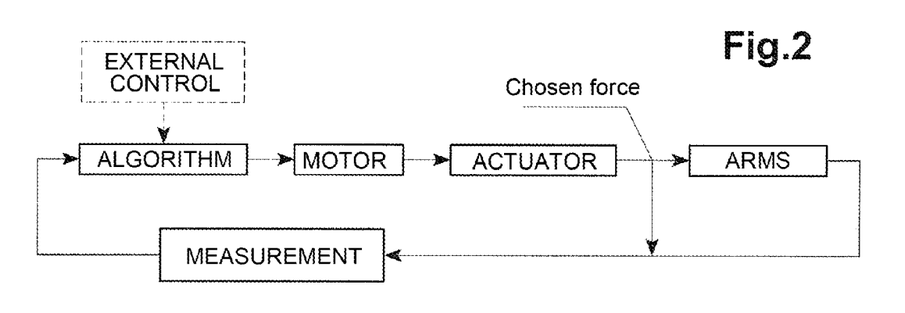
FIG. 2 shows a flowchart of a method of controlling the mechatronic device according to the invention.
Figure 3:
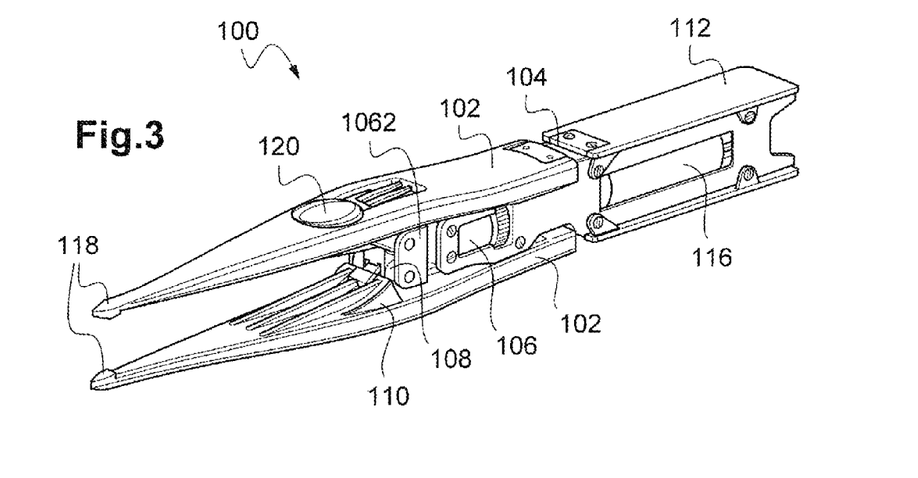
FIG. 3 shows a perspective view of a mechatronic device in accordance with one embodiment of the invention.
Figure 4:
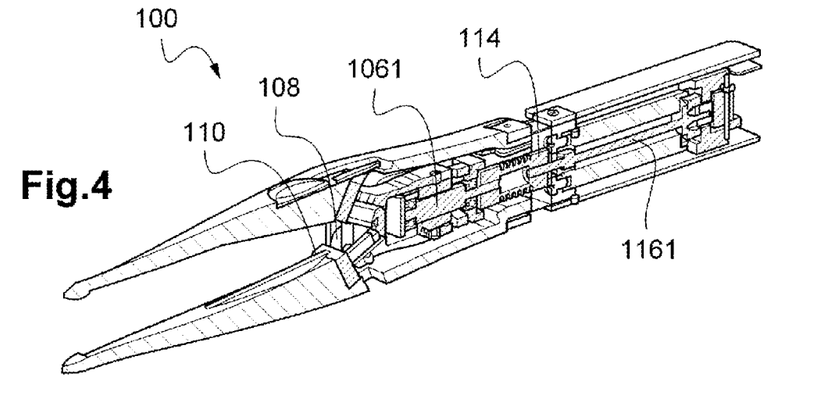
FIG. 4 shows a perspective view in section of the device from FIG. 3.
Figure 5:
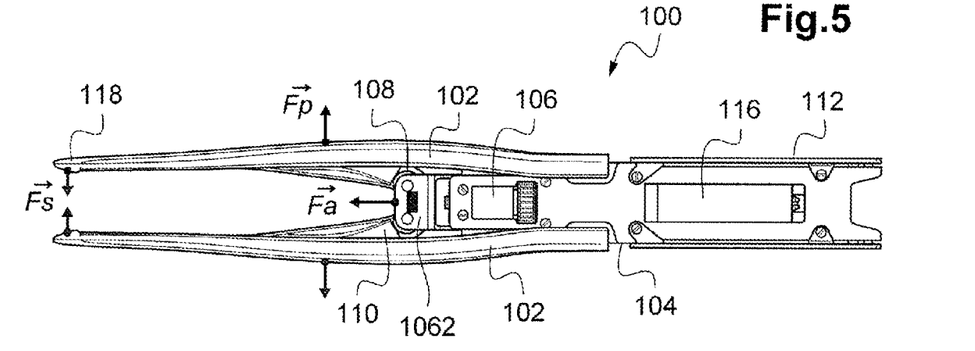
FIG. 5 shows a top view of the device from FIG. 3.

FIG. 2 shows a flowchart of a method of controlling the mechatronic device according to the invention. An EXTERNAL CONTROL operation comprises control by an operator or by a robotic system of drive parameter settings of a motor in accordance with variable criteria. An ALGORITHM operation transmits the drive parameters to a motor. The ALGORITHM operation notably comprises conversion calculations to generate and then to transmit to the motor parameters adjusted in accordance with the choices set during the EXTERNAL CONTROL operation. A MOTOR operation comprises the active operation of a motor in accordance with the parameter or parameters chosen during the EXTERNAL CONTROL operation and, where appropriate, adjusted during the ALGORITHM operation. The active operation of the motor in the MOTOR operation has the consequence of driving an actuator in movement in translation in an ACTUATOR operation. The driving of the actuator acts directly on arms of the mechatronic device by engaging a movement in rotation of same in the ARMS operation. The chosen force applied by the actuator to the arms is defined by the combination of the EXTERNAL CONTROL and ALGORITHM operations. In this way the operator or the robotic system is able to control the mechatronic device. The forces resulting from the driving of the actuator, positioning it and/or it acting on the arms can be measured by means of sensors during the ACTUATOR operation. Likewise, the forces resulting from the movement of the two arms, their respective positions and/or their action on an object can be measured by means of sensors during the ARMS operation. The ACTUATOR and ARMS operations are therefore actively controlled by the operator or the robotic system in a MEASUREMENT operation. The results of the measurements effected by the sensors during the MEASUREMENT active control operation are integrated into the calculations of the ALGORITHM operation in order to control the chosen force applied to the mechatronic device and thus to decorrelate the force of the operator with respect to grasping an object.

We now refer to FIGS. 3 to 7.

The mechatronic gripper 100 has the general appearance of straight tweezers. The gripper 100 has a general symmetry with respect to a longitudinal central axis. Two arms 102 extend longitudinally from a base 112 in a first direction. Each arm 102 comprises free ends 118. The arms 102 are mounted on the base 112 so as to be able to be moved toward each other by a movement in rotation. To this end, each arm 102 is mounted to rotate on the base 112. To be more precise, each arm 102 is fixed to the base 112 by a respective leaf spring 104. The gripper 100 therefore comprises two leaf springs 104. The leaf springs 104 are interchangeable in order to modify the stiffness of the gripper 100 if required.

The movement of the arms 102 toward each other by rotation results in a movement of the free ends 118 toward each other. The free ends 118 therefore form a gripper able to grasp objects. The two arms 102 generally have free ends 118 forming a gripper and are adapted to be moved toward each other by rotation from a rest position to an active position.

The gripper 100 is shaped to be handheld by an operator. To this end the gripper 100 includes a holding zone 120 on each arm. During use, an operator can notably rest a finger on each holding zone 120 in order to manipulate the gripper 100, for example by placing the index finger and the thumb of one hand on respective arms 102.

The base 112 accommodates a motor 116. The motor may be of DC electric motor type, which has a rotor of low inertia thanks to a stationary ferromagnetic core. In the present embodiment, the motor is the DCX10L EB KL 4.5V motor from MAXON MOTOR AG. That motor employs a so-called "coreless" technology based on permanent magnets. The energy performance and the dimensions of this type of motor are particularly suitable for the mechatronic device according to the invention. The motor is generally and preferably an electromagnetic motor the mobile part of which is constituted either by a magnet or by a coil.

The mechatronic gripper further comprises an actuator 106. The actuator 106 is advantageously a ball-screw 1061. In fact, ball-screws offer good performance in terms of minimizing friction. A ball-screw comprises a screw element and a nut element coupled to each other so that movement in translation of the nut drives movement in rotation of the screw, and vice versa. In the present embodiment, the actuator 106 is a 4×1 Carry Type "ZYI" ball-screw from EICHENBERGER GEWINDE AG. The performance in terms of friction and the dimensions of this type of actuator are particularly suitable for the mechatronic device according to the invention. It is a miniature ball-screw having a helix angle $\theta>4°$. The degree of freedom in rotation of the nut of the ball-screw is blocked.

Other types of actuators may be used. For example, actuators comprising a set of ball bearings moving with a helicoidal trajectory around a smooth rod may be used [for example: Roh'lix® Linear Actuators from ZERO-MAX, INC]. However, at present actuators of this type are generally bulky.

The actuator 106 is adapted to engage a movement in translation in both directions of the central longitudinal axis. In other words, the actuator 106 is adapted to engage a movement in translation both ways in the first direction: i.e. a push or a pull. This is achieved by means of the ball-screw. In fact, as mentioned above, the consequence of the rotation of the screw is movement in translation of the nut element of the ball-screw.

The motor 116 comprises a motor shaft 1161. The motor shaft 1161 is driven in rotation. The motor shaft 1161 is connected to a flexible coupling member 114. The flexible coupling member 114 is moreover connected to the actuator 106 and to be more precise to the screw element of the ball-screw 1061. The motor 116 therefore drives the ball-screw 1061 of the actuator 106 in rotation by way of the flexible coupling member 114. The flexible coupling member 114 mounted between the motor 116 and the actuator 106 makes it possible to alleviate any axis errors between the motor shaft 1161 and the ball-screw 1061.

The consequence of driving the ball-screw in rotation is movement in translation of the nut element of the screw 1061. To this end a head 1062 is provided on the actuator 106. The head 1062 can therefore exert forces on the mechatronic gripper 100 and more particularly on the arms 102.

To this end the movement in translation of the actuator 106, and more precisely of the head 1062, must be transformed into movement in rotation of the arms 102. To this end the gripper 100 comprises one or more cams. More generally, the actuator 106 has at least one first contact surface adapted to form a cam with at least one respective second contact surface situated on each arm 102.

More generally, when the gripper is closed by an operator (movement of the arms towards each other), the movement in translation of the nut element (head 1062) of the ball-screw is converted into rotation of the screw element (screw 1061) of the ball-screw: the impedance of this movement is then modulated by the motor 106. Obviously, the rotation of the screw element can also drive the movement in translation of the nut element.

The actuator 106 can therefore be the source of a force opposing the movement toward each other of the arms 102 and a force assisting the movement toward each other of the arms 102. A force opposing the movement toward each other is reflected in practice by the operator perceiving resistance on moving the arms (and therefore the free ends 118) toward each other. Conversely, a force assisting the movement toward each other is reflected in practice by the operator perceiving assistance during the movement toward each other of the arms (and therefore of the free ends 118).

In a very general way, the force exerted by the screw 1061 on the head 1062 is increased before being transmitted to the arms 102. It will nevertheless be noted that this is not the same type of force.

In one embodiment, the actuator 106 comprises rollers 108 forming the first surface. In this embodiment, each arm 102 comprises shoulders 110 projecting toward the opposite arm. The shoulders include planes inclined at an angle between approximately 35° and 75°. The cooperation between roller and shoulder enables transformation of the movement in translation of the actuator 106 into movement in rotation of the arms 102. The arrangement of the roller/shoulder assembly is a cam forming member.

In the present embodiment, each arm 102 includes two shoulders 110. The shoulders 110 are disposed on respective opposite sides of the arm, in the vicinity of the edges of the arm. The mechatronic gripper therefore includes four shoulders in total. In this embodiment, the actuator 106 carries four rollers 108, each roller being adapted to come into contact with a corresponding shoulder 110.

The actuator 106 can exert a force between 50 mN and 30 N. This results in the operator perceiving a force between 10 mN and 6 N. In practice, the actuator 106 can engage a push or a pull. Accordingly, the actuator 106 can strictly speaking exert a force between −30 N and 30 N.

For effective transformation of actuator movement in translation to arm movement in rotation, the first contact surface(s) remain engaged with the respective second contact surface(s). To this end, the applicant has surprisingly discovered that in the mechatronic device according to the invention magnetic components make it possible to establish a permanent and effective contact between the first contact surface(s) and the respective second contact surface(s), whilst addressing the energy requirements and sizing constraints.

Figure 6:
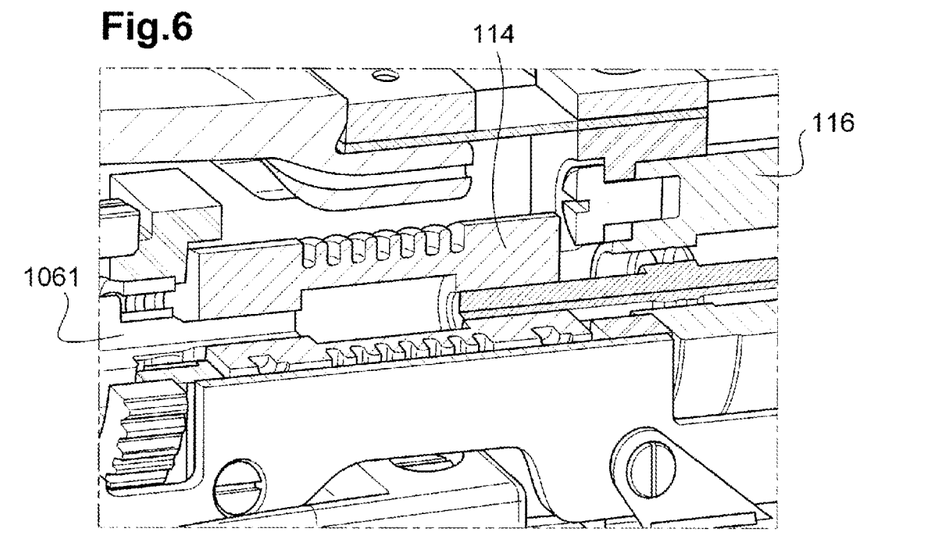
FIG. 6 shows a close-up perspective view of a first partial section of the device from FIG. 3.
Figure 7:
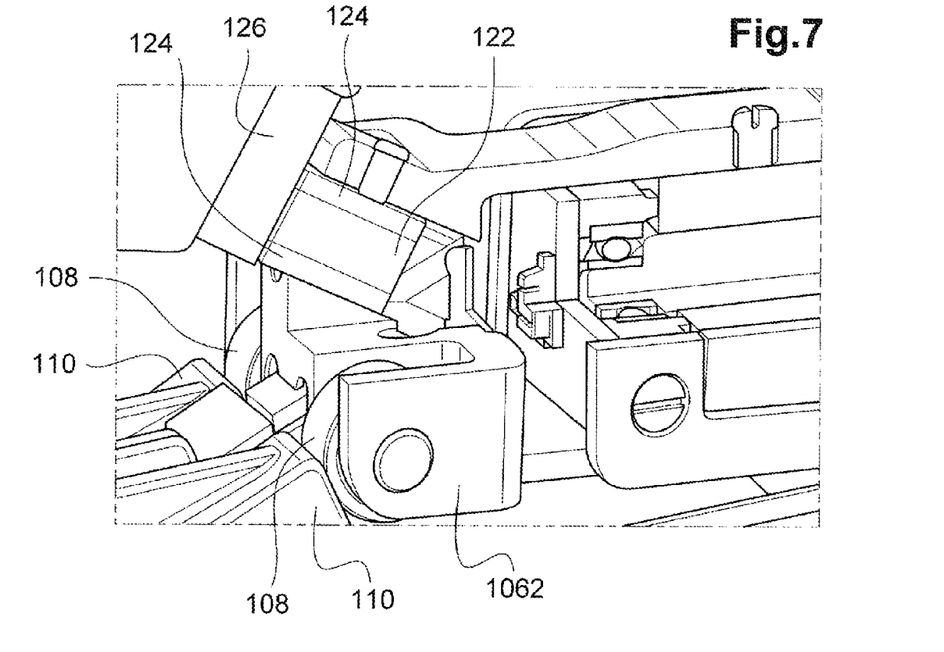
FIG. 7 shows a close-up perspective view of a second partial section of the device from FIG. 3.

In the present invention, the permanent contact between roller(s) 108 and shoulder(s) 110 is produced by means of a first magnetic component and a second magnetic component. Here the first magnetic component consists of a permanent magnet 122 sandwiched between ferromagnetic cores 124. Here the second magnetic component consists of a ferromagnetic receiver 126. This arrangement makes it possible to channel the magnetic field of the permanent magnet in order to generate a powerful contact force between roller(s) and shoulder(s).

The magnetic prestressing is generally provided by a circuit composed on the one hand of a permanent magnet on which are arranged high-permeability and low-saturation ferromagnetic material amplifiers and on the other hand of a receiver constituted of the same ferromagnetic material and being movable relative to the rest of the magnetic circuit. Accordingly, the connection and the contact between roller and shoulder (forming a bidirectional cam) is provided by the magnetic prestressing action.

The mechatronic device comprises control means enabling action on the actuator 106 and active control in real time thereof. This enables production of a movement in rotation of said arms that exerts a chosen gripper force in the active position. The control means may comprise a predefined force database stored in a memory. Accordingly, the chosen force applied during use of the gripper may be selected from those predefined forces.

In use, the mechatronic gripper is adapted to apply actively or automatically holding forces Fp, grasping forces Fs and forces Fa on the actuator. The forces are summarized in table 1. Four operating cases may be defined depending on the forces acting on the gripper 100 according to the invention.

TABLE 1

Different cases of operation of the mechatronic gripper 100

|  | 1st case | 2nd case | 3rd case | 4th case |
|---|---|---|---|---|
| $F_p$ Holding force | ≠0 | =0 | ≠0 | ≠0 |
| $F_s$ Grasping force | =0 | ≠0 | ≠0 | ≠0 |
| $F_a$ Force on actuator | ≠0 | ≠0 | ≠0 | =0 |

1st case: The operator perceives a force opposing the closing of the gripper without any physical object being manipulated. One application is notably in the simulation of grasping objects or in the virtual grasping of objects.

2nd case: The operator is able to grasp an object (by movement toward each other of the arms 102) without having to exert the slightest closing force with their fingers. One application is notably to the active control of grasping fragile objects.

3rd case: The grasping and holding forces are non-zero. One application is notably in the real time control grasping of objects. This is the most general case of operation. In fact, the other cases are nothing other than special cases of the present 3rd case, namely when one or more of the forces in play is or are zero.

4th case: The forces on the actuator are zero. The active system is deactivated. Under these conditions, the gripper 100 may be employed as standard tweezers.

The decoupling of the forces Fp and Fs is reflected in a defined function $f$ such that:

$f$ (forces Fp, Fs, Fa)=0

Figure 8:
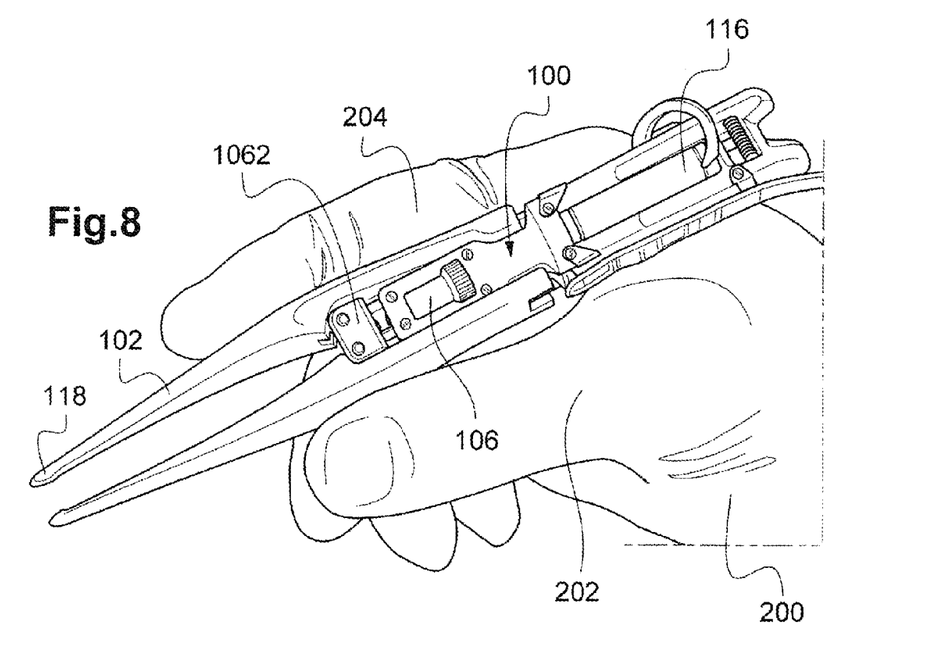
FIG. 8 shows a drawing of a mechatronic device handheld by an operator.

FIG. 8 shows a drawing of a mechatronic device 100 according to the invention. The arms 102 are handheld by an operator. The photograph shows a hand 200. The drawing shows a first (index) finger 204 placed on a first arm 102 and a second finger (thumb) 206 placed on the other arm 102. The motor 116 drives the actuator 106. The head 1062 therefore engages a movement in translation that acts directly on the movement away from each other and the movement towards each other of the arms 102 and therefore respectively on the opening and the closing of the gripper formed by the free ends 118.

The whole of the kinematic chain DRV., CONV., TRANS. and MANIP. constituted by the various elements of the mechatronic gripper is highly reversible so that no parasitic influence (such as friction or the inertia of the moving mechanical parts) comes to interfere with the holding force that it is wished to be transmitted to the fingers of the operator (or the grasping force that it is wished to be applied to an object). An advantage is that the elements constituting the kinematic chain have a high specific stiffness (ratio of stiffness to mass) in the direction of the movement.

Moreover, the mechatronic device can carry sensors measuring the force perceived by the fingers of the user and/or position sensors measuring the opening of the arms of the gripper and/or sensors enabling coordinates in space to be deduced (by measuring with the 6 degrees of freedom the position of the gripper in space).

The small overall size of the device according to the invention, its lightness (<40 g) and its ergonomics make it a portable mechatronic gripper offering a good grasp in the hand and more comfortable use than the prior art solutions. Moreover, the energy consumption of the device according to the invention is sufficiently low to enable it to be battery powered.

In summary, the invention provides a reversible miniature kinematic system that is compatible with implementation on gripper of small size such as tweezers. The kinematic system is notably composed of a low-inertia motor, a high-yield ball-screw and an assembly forming a magnetically prestressed cam. Sensors measuring forces and movements connected to a control system can complete that system. The small overall size and the geometry close to that of standard tweezers make it an intuitive device that is comfortable for an operator to use.

The mechatronic gripper according to the invention enables generation of opening and closing forces up to 6 N at the level of the fingers and 3 N at the ends of the arms, over a millimeter-scale travel of approximately 5 mm between the fingers and 10 mm at the end of the gripper. The gripper is moreover compatible with portability constraints such as compactness (144 mm×15 mm×22 mm), weight (approximately 40 g) and energy consumption. Trials have been carried out grasping virtual objects simulated by a computer.

Virtual object grasping tests have been carried out. The object simulation may be computed by a computer in particular. The operators had the impression of physically grasping an object by closing the arms of the gripper according to the invention. Virtual grasping is notably made possible by haptic feedback opposing the closing movement initiated by the operator.

Tests of active grasping of real objects with no effort on the part of the operator have also been carried out. The operators were able to grasp physical objects without exerting any force to close the gripper.

Additionally, diverse tests of manipulation by operators have been carried out. Trembling of the hands of the operators was compensated effectively in such a manner as to guarantee a constant grasping force. Thus, the gripper according to the invention enables active control of an operator's movements and clamping forces. Manipulations of objects on a sub-millimeter scale by operators are possible with the gripper according to the invention. Moreover, if the gripper is coupled to a robot, manipulations at the micrometric scale are possible using the gripper according to the invention.

What is claimed is:

1. A mechatronic device comprising two arms (102) extending generally from a base (112) in a first direction and shaped so as to be handheld by an operator, the two arms comprising free ends (118) forming a gripper and arranged to move closer together, by rotation, from a rest position to an active position, a motor (116) housed in the base, an actuator (106) mounted between the arms, and a means for controlling said actuator, the actuator (106) connected to the motor in a such a way as to be moved in translation in the first direction, the actuator having at least one first contact surface arranged to form a cam with at least one second respective contact surface situated on each arm (102), the at least one first contact surface remaining engaged with the respective at least one second contact surface, the means for controlling the actuator (106) being arranged to control said translation movement of the actuator in order to produce a rotational movement of said arms (102), that applies a chosen force of the gripper in its active position, wherein the chosen force is between 50 mN and 50 N.

2. The mechatronic device as claimed in claim 1, wherein said chosen force is selected from a force opposing rotation toward one another of said free ends and a force assisting rotation toward one another of said free ends.

3. The mechatronic device as claimed in claim 1, wherein the actuator (106) is disposed on a longitudinal axis and wherein said movement in translation of the actuator in the first direction is chosen from a movement of the actuator on the longitudinal axis in the first direction of that axis and a movement of the actuator on the longitudinal axis in the second direction of that axis.

4. The mechatronic device as claimed in claim 1, wherein the actuator (106) comprises a ball-screw.

5. The mechatronic device as claimed in claim 1, wherein the actuator (106) comprises at least one inclined plane, said at least one inclined plane forming said first contact surface, and wherein each arm comprises at least one rotatably mounted roller, said at least one roller forming the respective at least one second contact surface.

6. The mechatronic device as claimed in claim 1, further comprising a first magnetic component proximate to the at least one first contact surface and a second magnetic component proximate to the at least one second contact surface, the first and second magnetic components attracting each other so as to bring about at least a partial engagement between the at least one first contact surface and the respective at least one second contact surface.

7. The mechatronic device as claimed in claim 6, wherein the first and second magnetic components comprise independently of each other at least one of: a permanent magnet, a ferromagnetic body or an electromagnet.

8. The mechatronic device as claimed in claim 1, wherein the control means comprise a predefined force database stored in a memory and wherein the chosen force is selected from those predefined forces.

9. The mechatronic device as claimed in claim 1, wherein said free ends (118) of the arms comprise interchangeable tips.

10. A mechatronic device comprising two arms (102) extending generally from a base (112) in a first direction and shaped so as to be handheld by an operator, the two arms comprising free ends (118) forming a gripper and arranged to move closer together, by rotation, from a rest position to an active position, a motor (116) housed in the base, an actuator (106) mounted between the arms, and a means for controlling said actuator, the actuator (106) connected to the motor in a such a way as to be moved in translation in the first direction, the actuator having at least one first contact surface arranged to form a cam with at least one second respective contact surface situated on each arm (102), the at least one first contact surface remaining engaged with the respective at least one second contact surface, the means for controlling the actuator (106) being arranged to control said translation movement of the actuator in order to produce a rotational movement of said arms (102), that applies a chosen force of the gripper in its active position wherein the actuator (106) is connected to the motor (116) by means of a flexible coupling member (114).

11. A mechatronic device comprising two arms (102) extending generally from a base (112) in a first direction and shaped so as to be handheld by an operator, the two arms comprising free ends (118) forming a gripper and arranged to move closer together, by rotation, from a rest position to an active position, a motor (116) housed in the base, an actuator (106) mounted between the arms, and a means for controlling said actuator, the actuator (106) connected to the motor in a such a way as to be moved in translation in the first direction, the actuator having at least one first contact surface arranged to form a cam with at least one second respective contact surface situated on each arm (102), the at least one first contact surface remaining engaged with the respective at least one second contact surface, the means for controlling the actuator (106) being arranged to control said translation movement of the actuator in order to produce a rotational movement of said arms (102), that applies a chosen force of the gripper in its active position, wherein the actuator comprises at least one rotatably mounted roller (108), said at least one roller forming said first contact surface, and wherein each arm comprises at least one shoulder (110) projecting toward the opposite arm, said at least one shoulder forming the respective at least one second contact surface.

* * * * *